United States Patent [19]

Ratti

[11] Patent Number: 4,619,785
[45] Date of Patent: Oct. 28, 1986

[54] NOVEL SYNTHESIS ROUTE FOR BACAMPICILLIN

[75] Inventor: Luigi Ratti, Bergamo, Italy

[73] Assignee: Astra Lakemedel Aktiebolag, Sodertalje, Sweden

[21] Appl. No.: 507,717

[22] Filed: Jun. 23, 1983

[30] Foreign Application Priority Data

Jun. 29, 1982 [IT] Italy .............................. 22141 A/82

[51] Int. Cl.$^4$ .................. C07D 499/08; C07D 501/02
[52] U.S. Cl. ................................................. 540/318
[58] Field of Search ............... 260/239.1, 463; 544/30, 544/22, 23, 24, 25, 26, 27, 28, 29

[56] References Cited

U.S. PATENT DOCUMENTS

| | | |
|---|---|---|
| Re. 29,650 | 5/1978 | Ferres ............................... 260/239.1 |
| 3,316,247 | 4/1967 | Fosker et al. .................... 260/239.1 |
| 3,325,479 | 6/1967 | Fosker et al. .................... 260/239.1 |
| 3,697,507 | 10/1972 | Frederiksen et al. ............ 260/239.1 |
| 3,873,521 | 3/1975 | Ekström et al. ................. 260/239.1 |
| 4,342,772 | 8/1982 | Godtfredsen et al. ........... 260/239.1 |

FOREIGN PATENT DOCUMENTS

| | | |
|---|---|---|
| 309683 | 8/1973 | Austria . |
| 784800 | 10/1972 | Belgium . |
| 784698 | 12/1972 | Belgium . |
| 866093 | 10/1978 | Belgium . |
| 187312 | 4/1978 | Czechoslovakia . |
| 0054512 | 6/2982 | European Pat. Off. . |
| 2161420 | 7/1972 | Fed. Rep. of Germany . |
| 1795701 | 10/1973 | Fed. Rep. of Germany . |
| 1795702 | 10/1973 | Fed. Rep. of Germany . |
| 2423490 | 2/1975 | Fed. Rep. of Germany . |
| 3008257 | 9/1980 | Fed. Rep. of Germany . |
| 64695 | 8/1964 | South Africa . |
| 7313549 | 10/1973 | Sweden . |
| 7505741 | 5/1975 | Sweden . |
| 991586 | 5/1965 | United Kingdom . |
| 1033257 | 6/1966 | United Kingdom . |
| 1302917 | 1/1973 | United Kingdom . |
| 1332508 | 10/1973 | United Kingdom . |
| 1347979 | 2/1974 | United Kingdom . |
| 1363506 | 8/1974 | United Kingdom . |
| 1364672 | 8/1974 | United Kingdom . |
| 1377817 | 12/1974 | United Kingdom . |
| 1390754 | 4/1975 | United Kingdom . |
| 1425571 | 2/1976 | United Kingdom . |
| 1426717 | 3/1976 | United Kingdom . |
| 1426869 | 3/1976 | United Kingdom . |
| 1427139 | 3/1976 | United Kingdom . |
| 1433131 | 4/1976 | United Kingdom . |
| 1443738 | 7/1976 | United Kingdom . |

OTHER PUBLICATIONS

Noller Chemistry of Organic Compounds, 3rd Ed., pp. 185–186, Philadelphia, Saunders, 1965.
Chemical Abstracts, 85:108,630Z (Spanish Pat. No. 411,934), (1976).
Chemical Abstracts, 90:152209w, (1979).
Chemical Abstracts, 90:127547x, (1979).
Chemical Abstracts, 91:74633j, (1979).
Chemical Abstracts, 92:111279s, (1980).
Chemical Abstracts, 93:168262f, (1980).
Angew Chem., 74 (1962) No. 21, p. 873.

*Primary Examiner*—Natalie Trousof
*Assistant Examiner*—Vera C. Clarke
*Attorney, Agent, or Firm*—Brumbaugh, Graves, Donohue & Raymond

[57] ABSTRACT

The novel compound α-bromodiethylcarbonate, its use in the preparation of 1-ethoxycarbonyloxyethyl esters of penicillins and cephalosporins, in particular bacampicillin, and improvements in the method for preparing such esters.

10 Claims, No Drawings

NOVEL SYNTHESIS ROUTE FOR BACAMPICILLIN

FIELD OF THE INVENTION

This invention relates to a novel method of manufacturing the 1-ethoxycarbonyloxyethyl ester of the 6-(D-(−)-α-amino-α-phenylacetamido)penicillanic acid of the formula I:

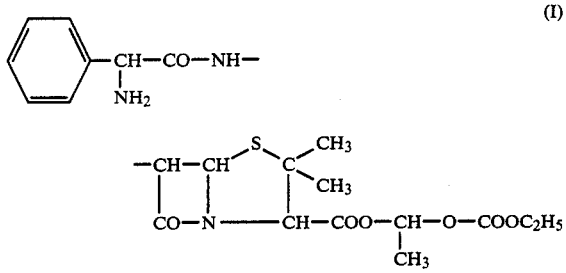

Furthermore, the invention relates to the novel compound α-bromodiethylcarbonate, which with great advantage is used in the said novel method for preparing bacampicillin of the formula I, and which in a more general sense is also used with great advantage in the preparation of the ethoxycarbonyloxyethyl ester of 6-aminopenicillanic acid, penicillins and cephalosporin the use of α-bromodiethylcarbonate in the preparation of the ethoxycarbonyloxyethyl ester of 6-aminopenicillanic acid, penicillins such as penicillin G, penicillin V and ampicillin, and cephalosporin.

improvements in the process for preparing ethoxycarbonyloxyethyl esters of 6-aminopenicillanic acid, penicillins and cephalosporin.

The substance I concerned is an ampicillin ester which is extremely important from the therapeutic point of view since it is well absorbed when administered orally and gives much higher blood levels of ampicillin than ampicillin itself.

This ester is isolated in the form of a hydrochloride and is known as bacampicillin hydrochloride.

BACKGROUND OF THE INVENTION

On the basis of previous known processor (cf. Belgian patent No. 772723), bacampicillin hydrochloride can be synthesized by the two following methods:

(A) Reaction of potassium benzylpenicillin with α-chlorodiethylcarbonate in organic solvents or in an aqueous solution of 70% dioxane in the presence of sodium bicarbonate. The 1-ethoxycarbonyloxyethyl ester of benzylpenicillin which is obtained is subjected to the reaction of removing the phenylacetic chain, via the iminochlorideimino-ether, in order to obtain the 1-ethoxycarbonyloxyethyl ester of the 6-aminopenicillanic acid, which is isolated as the hydrochloride.

By subsequent condensation of the latter intermediate with D-(−)-α-phenylglycine, the compound according to formula I is obtained.

(B) Esterification reaction of the 6-(D-(−)-α-azido-α-phenylacetamido)penicillanic acid with α-chlorodiethylcarbonate in a polar solvent.

Subsequently, by catalytic hydrogenation of the 1-ethoxycarbonyloxyethyl ester of the 6-(D-(−)-α-azido-α-phenylacetamido)penicillanic acid the compound according to formula I is obtained.

As one can see, these methods are rather complex since they involve the use of numerous raw materials and lengthy processing times.

THE INVENTION

A prime object of this invention is to provide a method of preparing the active substance concerned which is easier to carry out and industrially more advantageous. A more specific object of this invention is to provide a method of preparing bacampicillin using ampicillin as starting material, with considerable simplification of the said method and obtaining a high degree of purity of the desired product.

The invention also provides the novel compound α-bromodiethylcarbonate, the use of α-bromodiethylcarbonate in the preparation of the ethoxycarbonyloxyethyl ester of 6-aminopenicillanic acid, penicillins such as penicillin G, penicillin V and ampicillin and cephalosporins, and improvements in the process for preparing ethoxycarbonyloxyethyl esters of 6-aminopenicillanic acid, penicillins and cephalosporin.

α-bromodiethylcarbonate is used with great advantage as a reactant in these esterification processes. The use of α-bromodiethylcarbonate leads to particularly high yield and high purity of the final products such as bacampicillin.

It is possible to achieve the said prime object with a method of preparing the 1-ethoxycarbonyloxyethyl ester of the 6-(D-(−)-α-amino-α-phenylacetamido)-penicillanic acid having the following formula:

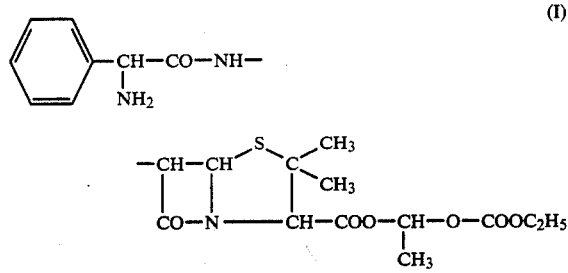

characterized by the following stages:

(a) reacting of ampicillin, preferably in the form of an alkaline salt, with a reactive derivative of actoacetic acid to form the corresponding enamine having the following formula:

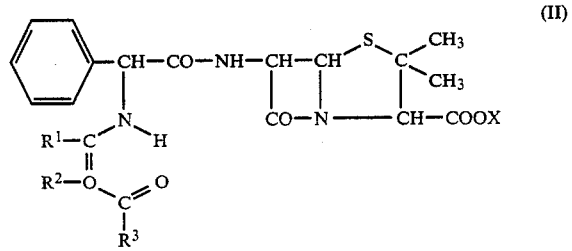

where:
$R^1$ represents an alkyl group containing 1 to 4 carbon atoms, a substituted or unsubstituted aryl group or an aralkyl group;
$R^2$ represents hydrogen, an alkyl group containing 1 to 4 carbon atoms, a substituted or unsubstituted aryl group or an arylkyl group;

R³ represents an alkyl group containing 1 to 4 carbon atoms, a substituted or unsubstituted aryl group, an arylkyl group, an alkoxy group containing 1 to 4 carbon atoms, an aryloxy group or an amino group, and X represents an alkali metal, an alkaline-earth metal or an organic base;

(b) reaction of the resulting intermediate with an α-bromo-diethylcarbonate having the following formula:

$$Br-CH-O-COOC_2H_5 \quad (III)$$
$$\phantom{Br-}\,|$$
$$\phantom{Br-}CH_3$$

to form the corresponding ester having the following formula:

(IV)

[Structure showing phenyl-CH-CO-NH- connected to R¹-C=N-H, R²-C=C=O with R³, then -CH-CH-S-C(CH₃)(CH₃), CO-N-CH-COO-CH(CH₃)-O-COOC₂H₅]

where R¹, R² and R³ have the same significance as above and (c) hydrolysis in an acid medium, obtaining the compound according to formula (I).

The esterification reaction between the compounds II and III can be carried out with or without an esterification catalyst present.

The addition of a catalyst at this stage considerably shortens the reaction times and provides higher yields of the product with a greater degree of purity.

For this prupose the following substances can be used as catalysts: quaternary ammonium salts, for example tetrabutylammonium bromide, the bromides or iodides of alkali metals and cyclic ethers.

The catalyst may be used in an amount which varies from 0.005 to 0.10 moles per mole of compound III to amounts which are equimolar with the compound III. In a preferred embodiment tetrabutylammonium bromide is used in an amount of from 0.01 to 0.10 moles per mole of compound III.

The invention also includes an embodiment of the process outlined above for the preparation of bacampicillin which comprises reacting a compound of the formula II with a compound of the formula $$Z-CH-O-COO-C_2H_5 \quad (V)$$
$$\phantom{Z-}\,|$$
$$\phantom{Z-}CH_3$$

wherein Z is Cl or I, which embodiment is characterized in that the process is carried out in the presence of a catalytic amount of a catalyst as specified above. The catalyst is suitably used in an amount of from 0.005 to 0.10 moles per mole of compound V.

Illustrative examples of the radicals R¹, R² and R³ are:

| alkyl: | $CH_3$, $C_2H_5$, n-$C_3H_7$, i-$C_3H_7$, n-$C_4H_9$ |
|---|---|
| alkoxy (R³ only): | $OCH_3$, $OC_2H_5$, $OCH_2CH_2CH_3$, $OCH(CH_3)_2$, $O(CH_2)_3CH_3$ |
| aryl: | [phenyl ring] |
| substituted aryl: | phenyl substituted with halogen such as Cl and Br |
| aryloxy: | -O-[phenyl ring] |
| aralkyl: | -CH₂-[phenyl ring] |

The radical X is selected among groups which are well known in the art, for example alkali metal: Na, K alkaline earth metals: Ca, Mg organic base: organic bases which are known in the synthesis of penicillins, e.g. tertiary ammonium groups, triethylamine, ethylpiperidine and methylmorpholine.

In the preferred embodiment of the invention, the group protecting the amino group of the ampicillin is a 1-methoxy-carbonyl-propen-2-yl group or a 1-ethoxy-carbonyl-propen-2-yl group for which the preferred intermediate is the sodium or potassium salt of the N-(-1-methoxy-carbonylpropen-2-yl) penicillanic acid respectively N-(1-ethoxy-carbonylpropen-2-yl) penicillanic acid according to formula II (R¹=methyl; R²=methyl; R³=methoxy or ethoxy and X=Na or K).

The intermediate IV is stable in a neutral or alkaline medium, whereas in an acid medium it is possible to remove the group protecting the amino group simply, quickly and selectively.

The group protecting the amino group of the ampicillin can be selected e.g. from the groups mentioned in the British patent specification No. 991586, and from other groups which are known in the art.

The α-bromodiethylcarbonate, compound III, which is a novel compound and as such included in the scope of the invention may be prepared by reacting the corresponding α-chlorodiethylcarbonate with sodium bromide as is exemplified in Example 1 below.

More specifically, therefore, the process method according to a preferred embodiment of this invention, comprises the following stages:

transformation of ampicillin trihydrate in a polar solvent, for example N,N-dimethylformamide, into a salt thereof, for example potassium, and subsequent formation of the corresponding enamine (II) by reaction with a derivative of acetoacetic acid, for example methyl acetoacetate.

addition of an esterification catalyst, preferably tetrabutylammonium bromide addition of α-bromdiethylcarbonate to the reaction mixture to form the 1-ethoxycarbonyloxyethyl ester of the ampicillin in the form of the enamine (IV).

hydrolysis of the protective group with HCl diluted in an organic solvent, for example n-butyl acetate/water.

recovery of the bacampicillin hydrochloride by saturation in the aqueous phase, for example with sodium chloride and extraction with a suitable solvent, for example n-butyl acetate.

concentration of the solution at low pressure in n-butyl acetate in order to crystallize the product to a high level of purity, the product then being isolated by filtration.

Among the main advantages of the process according to the invention, the principal one is that, by this process, it is possible to obtain bacampicillin hydrochloride practically in one operation and with a high degree of purity.

In fact the impurities which are present in the product obtained by the process according to the present invention are negligible as compared with the known processes of the previous state of the art.

Another equally important advantage is that ampicillin trihydrate is used as the starting material, this being a known antibiotic which is easily obtainable in pure form and at low cost.

The intermediate (II) can be easily prepared as described for example in British patent specification 991586 with a yield of over 95% by reaction of ampicillin trihydrate with methyl or ethyl acetoacetate, 10 to 50% more than the stoichiometric ratio, in the presence of an organic base or an alkali metal carbonate, for example potassium carbonate.

The intermediate (II) can be isolated and added to the esterification reaction in solid form. Or, without isolation of the intermediate (II), the esterification reaction can be effected in the same solvent in which the reaction for the formation of enamine (II) took place.

The reaction for the formation of ampicillin enamine (II) is conducted in an aprotic polar solvent, such as N,N-dimethylacetamide, N,N-dimethylformamide, dimethoxyethane, dimethylsulphoxide, tetrahydrofuran or dioxane.

To complete the reaction, it is sufficient to leave the components of the mixture in contact at a temperature between 0° C. and 60° C., preferably between 20° C. and 30° C., for 2 to 8 hours, preferably 3 hours.

The compound II can be prepared via acylation of 6-aminopenicillanic acid with a corresponding enamine derivative of phenylglycine to the formation of the compound II which thereafter can be esterified directly and converted to bacampicillin with isolation of the compound II.

The esterification reaction after the addition of the α-bromdiethylcarbonate to the said mixture, takes place at a temperature between 15° C. and 80° C., preferably between 45° C. and 55° C., for a period of time from 1 hour to 24 hours, preferably from 5 to 10 hours.

The esterification reaction is suitably carried out in an organic solvent such as methylene chloride or acetone, dimethylacetamide, dimethylformamide and dimethylsulfoxide, or in a mixture of organic solvents. It is possible to use also organic solvent containing water. The use of esterification catalyst is desirable when acetone is used as solvent for the esterification reaction.

In the easiest and most suitable conditions for industrial purposes, the esterified enamine (IV) is isolated by dilution of the reaction mixture with water and subsequent extraction with a suitable solvent which is immiscible with water, for example n-butyl acetate.

The acetate phase is agitated with a dilute solution (0.2-0.3N) of HCl until the protective group is completely hydrolysed, which requires a contact time of 2 to 8 hours, preferably 4-5 hours, at ordinary temperatures.

By addition of sodium chloride, compound (I) separates out from the aqueous phase in the form of the hydrochloride, which is extracted with a suitable solvent, for example n-butyl acetate.

By concentrating the organic phase at low pressure at a temperature of 40° C. until a small volume remains, crystallization of the product according to formula (I) takes place.

The crystalline product is isolated by filtration, washing and vacuum drying.

The following examples illustrate the present aspects of the invention without limiting it in any way.

EXAMPLE 1

Preparation of α-bromdiethylcarbonate

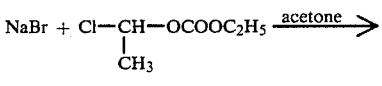

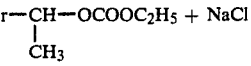

Sodium bromide (102.9 g) dissolved in aceton (600 ml) was reacted for 2-3 hours at ambient temperature (20°-25° C.) with α-chlorodiethylcarbonate (152.6 g) dissolved in 100 ml of acetone. The mixture was then concentrated under vacuum at low temperature, max. 35° C., until a semi-solid mass was obtained. The reaction mixture was then partitioned with H₂O/ethyl ether. The aqueous phase was separated and was then extracted twice with 400 ml of ethyl ether.

The combined organic phases containing the α-bromdiethylcarbonate were washed with
800 ml of H₂O
1000 ml of 1% sodium metabisulphate aqueous solution
1000 ml of NaCl saturated solution The organic phase was dried over Mg sulphate, and then concentrated under vaccum at low temperature, max. 35° C. to give The title product (60%) in the form of a liquid which initially was colourless or slightly yellow-brown.

It was used directly in the esterification step according to Example 2 below.

EXAMPLE 2

25.08 g (0.181 m) of finely ground anhydrous potassium carbonate are suspended in 200 ml of N,N-dimethylacetamide and 32.4 ml (0.3 m) of methyl acetoacetate and 60.4 g (0.15 m) pf ampicillin trihydrate are added.

The mixture is maintained under fast agitation for 5 hours at 20° C.-25° C.; after this time 46.1 g (0.234 m) of bromdiethylcarbonate, 6 g (0.02 m) of tetrabutyl ammonium bromide and 100 ml of N,N-dimethylacetamide are added.

It is heated under agitation for 10 hours at 40° C.-42° C.; the reaction mass is poured into a mixture consisting of 1200 ml of water and 400 ml of n-butyl acetate.

The aqueous phase is collected and extracted with another 100 ml of n-butyl acetate.

The reunited organic phases are washed twice with 100 ml of water each time. 150 ml N HCl and 370 ml of water are added to the organic phase which is subjected to agitation; it is left under agitation at 22° C.–23° C. for 4 hours.

The aqueous phase is collected and the organic phase is extracted with 100 ml of water.

The reunited aqueous phases are brought to pH 4 with a 10% aqueous solution of $Na_2CO_3$, then bleaching carbon is added to them and they are filtered.

300 ml of n-butyl acetate and 80 g of sodium chloride are added to the aqueous filtrate.

The organic phase is separated and the aqueous phase is extracted with 200 ml of n-butyl acetate.

The reunited phase in n-butyl acetate are concentrated at low pressure at 40° C. to a volume of approximately 300 ml. The product is left to crystallize for 15 hours at +5° C.

It is filtered, washed with n-butyl acetate (100 ml) and ethyl acetate (100 ml). It is vacuum dried at 40° C. for 24 hours.

Yield: 54.2 g (72%) of the 1-ethoxycarbonyloxyethyl ester of the 6-(D(−)-α-amino-α-phenylacetamido)-penicillanic acid with m.p. 160°-2° C. (d) and characteristics conforming to the authentic hydrochloride sample.

EXAMPLE 3

36.4 g (0.075 m) of potassium N-(1-methoxycarbonyl-propen-2-yl)-6-[D(−)-α-amino-α-phenylacetamido]-penicillate are added to a solution of 17.8 g (0.116 m) of α-chlorodiethylcarbonate and 3 g (0.01 m) of tetrabutylammonium bromide in 150 ml of N,N-dimethylformamide. Under agitation the temperature is raised to 45° C. and maintained at 45° C.–50° C. for 5 hours.

When heating is completed, the reaction mixture is poured into a mixture comprising 300 ml of a 14% aqueous sodium chloride solution and 600 ml of n-butyl acetate. The mixture is agitated for 10 minutes, then the organic phase is separated and the aqueous phase is extracted with 100 ml of n-butyl acetate. The reunited organic phases, after two washings with 75 ml of 14% sodium chloride aqueous solution, are concentrated at low pressure until an oil is obtained.

The oil is mixed with 200 ml of tetrahydrofuran and 100 ml of water; the solution obtained (pH 4.8) is brought under agitation to pH 1.5 by adding, in all, 12 ml of 6N HCl in 1 hour.

After leaving the solution to stand for another hour at ordinary temperature, the tetrahydrofuran is removed at low pressure at 40° C., 150 ml of n-butyl acetate are added to the remaining aqueous phase (150 ml) and then 15 g of sodium chloride are added.

The organic phase is separated and the aqueous phase is extracted with 100 ml of n-butyl acetate.

The reunited organic phases are concentrated under vacuum at 40° C. to a volume of 120 ml.

The product is left to crystallize for 15 hours at 5° C.

It is then filtered, washed with n-butyl acetate (50 ml) and ethyl acetate (50 ml).

It is vacuum dried at 40° C.

The following is obtained: 25.2 g (66.9%) of the 1-ethoxycarbonyloxyethyl ester of the 6-(D-(−)-α-amino-α-phenylacetamido)penicillanic acid hydrochloride with m.p. 160°-2° C.

Analytical determinations:

Titre: 97.82%.
Rotatory power: +166.3° (c=1, EtOH95°).
pH: 4.05 (2% aqueous solution).
Moisture content: 0.82%.
Residual solvents: ethyl acetate 0.45; n-butyl acetate 0.98%.
IR and NMR spectra are standard.
Residual ampicillin: 0.06%.

EXAMPLE 4

16.2 ml (0.15 m) of methyl acetoacetate and 30.2 g (0.075 m) of ampicillin trihydrate are added to a suspension of 12.54 g (0.0907 m) of finely pulverized anhydrous potassium carbonate in 100 ml of N,N-dimethylformamide.

It is maintained with agitation at 22° C.–23° C. for 3 hours and after this time considerable fluidization of the mass can be observed.

17.8 g (0.117 m) of α-chloro-diethylcarbonate, 3 g (0.01 m) of tetrabutylammoniumbromide and 50 ml of N,N-dimethylformamide are now added in that order.

The mixture is heated under agitation for 5 hours at 45°C.–50° C., then left to stand at +5° C. for 15 hours.

The reaction mass is poured into a mixture consisting of 600 ml of water and 200 ml of n-butyl acetate and it is agitated until a complete solution is obtained, the aqueous phase is collected and extracted with another 50 ml of n-butyl acetate.

The reunited organic phases are washed twice with 50 ml of water each time. 75 ml of N HCl and 185 ml of water are added to the organic phase subjected to agitation; it is left under agitation at 22° C.–23° C. for 4 hours.

The aqueous phase is collected and the organic phase is extracted with 50 ml of water. The reunited aqueous phase are brought to pH4 with a 10% aqueous solution of $Na_2CO_3$, then bleaching carbon is added to them and they are filtered.

150 ml of n-butyl acetate and 40 g sodium chloride are added to the aqueous filtrate.

The organic phase is separated and the aqueous phase is extracted with 100 ml of n-butyl acetate.

The reunited phases in butyl acetate are concentrated at low pressure at 40° C. to a volume of approximately 150 ml.

The product is left to crystallize for 15 hours at +5° C.

It is filtrated, washed with n-butyl acetate (50 ml) and ethyl acetate (50 ml).

It is dried under a vacuum of 10 mm Hg in the presence of moisture at 25° C. for 24 hours.

Yield: 20.8 g (55%) of the 1-ethoxycarbonyloxyethyl ester of the 6-(D(−)-α-amino-α-phenylacetamido)-penicillanic acid hydrochloride with m.p. 159°–161° C. and characteristics conforming to an authentic sample.

EXAMPLE 5

A mixture of 160 ml acetone, 22.6 g (0.075 mol) of the potassium salt of D(−)-N-methoxycarbonylpropen-2-yl-aminophenylacetic acid, 6.9 ml (0.088 mol) ethyl chloroformate and 3 drops of N-methylmorpholine, is stirred for 15 minutes at a temperature of −20°−−30° C. To this reaction mixture a solution of 16.2 g 6-aminopenicillanic acid, dissolved in 35 ml water through the gentle addition of 7.6 g (0.075 mol) triethylamine with agitation, is added in one portion, after which the mixture is diluted with 90 ml acetone and chilled to −20° C.

After stirring for 45 minutes, without any additional cooling, 23.4 g (0.117 mol) of α-bromodiethylcarbonate, 3 g (0.01 mol) or tetrabutylammonium bromide and 250 ml of N,N-dimethylformamide are added in that order. The mixture is stirred for 18 hours at 25° C. After that time the reaction mass is poured into a mixture consisting of 600 ml of water and 200 ml of n-butyl acetate and it is agitated until a complete solution is obtained. The aqueous phase is collected and extracted with another 50 ml of n-butyl acetate.

The reunited organic phases are washed twice with 50 ml of water each time. 185 ml of water is added to the organic phase and 1 N HCl is added dropwise with agitation to a pH of 1.9. The mixture is left under agitation at 22°-23° C. for 4 hours.

The aqueous phase is colleceted and the organic phase is extracted with 50 ml of water. The reunited aqueous phases are brought to pH 4 with a 10% aqueous solution of $Na_2CO_3$, active carbon is added to them and they are filtered. 150 ml of n-butyl acetate and 40 g of sodium chloride are added to the aqueous filtrate.

The organic phase is separated and the aqueous phase is extracted with 100 ml of n-butyl acetate. The reunited phases in butyl acetate are concentrated at low pressure at 40° C. to a volume of approximately 150 ml. The product is left to crystallize for 15 hours at +5° C.

It is filtered, washed with n-butyl acetate (25 ml) and ethyl acetate (25 ml). It is dried under a vacuum of 10 mm Hg at 25° C. for 24 hours.

Yield: 1.17 g of the 1-ethoxycarbonyloxyethyl ester of 6-(D(−)-α-amino-α-phenylacetamidopenicillanic acid hydrochloride with m.p. 159°-161° C. and characteristics (NMR, TLC) conforming to an authentic sample.

EXAMPLE 5a

The procedure of example 5 was repeated with the difference that the 6-aminopenicillanic acid was dissolved in 20 ml water instead of in 35.

Yield: 1.05 g of the ethoxycarbonyloxyethyl ester of 6-(D(−)-α-amino-α-phenylacetamidopenicillanic acid hydrochloride as a white crystalline powder with m.p. 148°-151° C., with decomposition, and characteristics (TLC, IR) conforming to an authentic sample.

EXAMPLE 6

6.25 g (0.045 m) of finely ground anhydrous potassium carbonate are suspended in 50 ml of dimethyl sulphoxide and 8.1 ml (0.075 m) of methyl acetoacetate and 15.1 g (0.0375 m) of ampicillin trihydrate are added.

The mixture is maintained under fast agitation for 5 hours at 20° C.-25° C.; after this time 11.5 g (0.059 m) of bromodiethylcarbonate and 25 ml of dimethyl sulphoxide are added.

It is heated under agitation for 17 hours at 35°-37° C.; the reaction mass is poured into a mixture consisting of 300 ml of water and 100 ml of n-butyl acetate.

The aqueous phase is collected and extracted with another 100 ml of n-butyl acetate.

The reunited organic phases are washed twice with 25 ml of water each time.

92.5 ml of water and NHCl (7.0 ml) to a pH of 1.9 are added to the organic phase which is subjected to agitation; it is left under agitation at 22° C.-23° C. for 2,5 hours.

The aqueous phase is collected and the organic phase is extracted with 25 ml of water.

The reunited aqueous phases are brought to pH 4 with 10% aqueous solution of $Na_2CO_3$, then active carbon is added to them and they are filtered.

75 ml of n-butyl acetate and 37 g of sodium chloride are added to the aqueous filtrate.

The organic phase is separated and the aqueous phase is extracted with 50 ml of n-butyl acetate.

The reunited phases in n-butyl acetate are concentrated at low pressure at 40° C. to a volume of approximately 75 ml. The product is left to crystallize for 15 hours at +5° C.

It is filtrated, washed with n-butyl acetate (25 ml) and ethyl acetate (25 ml). It is vacuum dried at 40° C. for 3 hours.

Yield: 1.9 g (10%) of the 1-ethoxycarbonyloxyethyl ester of the 6-(D(−)-α-amino-α-phenylacetamido)-penicillanic acid with m.p. 160°-162° C. and characteristics conforming to an authentic sample of the hydrochloride (e.g. IR:V 1790 cm$^{-1}$, β-lactam carbonyl).

The compound α-bromodiethylcarbonate, novel methods for the preparation thereof, and its use in the preparation of esters of 6-aminopenicillanic acid, penicillins and cefalosporins is disclosed in the British patent application no. 8226751 filed Sept. 20, 1982, no. 8228622 filed on Oct. 6, 1982, no. 8232629 filed on Nov. 16, 1982, and no. 8300331 filed on Jan. 7, 1983, all in the name of Palmer Research Limited. The content of the said British patent application is hereby incorporated by reference in the present application. Also the content of the corresponding U.S. patent application Ser. No. 507,716 titled "Novel intermediates and improvements in the preparation of antibiotics" in the name of D. R. Palmer and R. G. Tyson which is filed concurrently herewith and which is based on and claims priority from the said four British patent applications is hereby incorporated by reference in the present specification.

What I claim is:

1. Process for the preparation of the 1-ethoxycarbonyloxyethyl ester of the 6-(D-(−)-α-amino-α-phenylacetamido)penicillanic acid with the formula:

$$\begin{array}{c} \phantom{X} \\ \text{C}_6\text{H}_5-\text{CH}-\text{CO}-\text{NH}- \\ | \\ \text{NH}_2 \end{array} \quad (I)$$

$$-\text{CH}-\text{CH} \overset{S}{\underset{}{\diagdown}} \text{C} \overset{\text{CH}_3}{\underset{\text{CH}_3}{\diagup}}$$

$$\text{CO}-\text{N}-\text{CH}-\text{COO}-\underset{\underset{\text{CH}_3}{|}}{\text{CH}}-\text{O}-\text{COOC}_2\text{H}_5$$

characterized by steps of:
(a) in the presence of a material selected from the group consisting of an organic base and an alkaline carbonate in an aprotic solvent selected from the group consisting of N,N-dimethylacetamide, N,N-dimethylformamide, dimethoxyethane, dimethylsulphoxide, tetrahydrofuran and dioxane at a temperature between 0° C. and 60° C. for between 2 to 8 hours reacting ampicillin, or an alkaline salt, with a reactive derivative of acetoacetic acid to form the corresponding enamine with the formula:

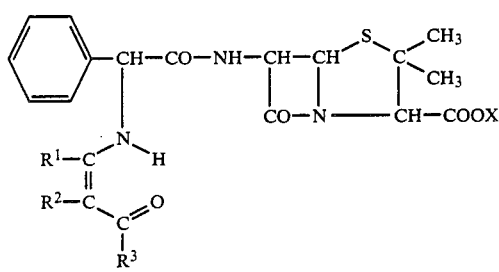 (II)

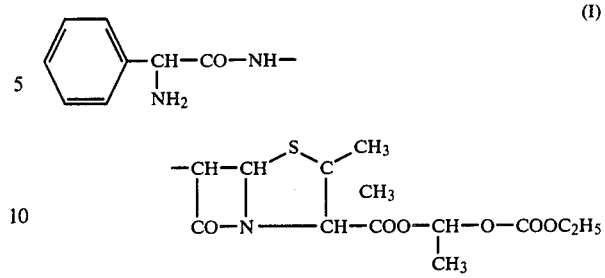 (I)

wherein R¹ represents an alkyl group containing 1–4 carbon atoms, a substituted or non-substituted aryl group or an aralkyl group; R² represents hydrogen, an alkyl group containing 1–4 carbon atoms, a substituted or non-substituted aryl group or an aralkyl group; R³ represents an alkyl group containing 1–4 carbon atoms, a substituted or non-substituted aryl group, an aralkyl group, an alkoxy group containing 1–4 carbon atoms, an aryloxy group or an amine group, and X represents an alkali metal, an alkaline earth metal or an organic base;

(b) reacting the resulting intermediate with α-bromo-diethyl carbonate with the formula:

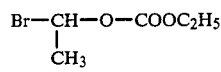 (III)

at a temperature of 15°–80° C. for 1–24 hours to form the corresponding ester with the formula:

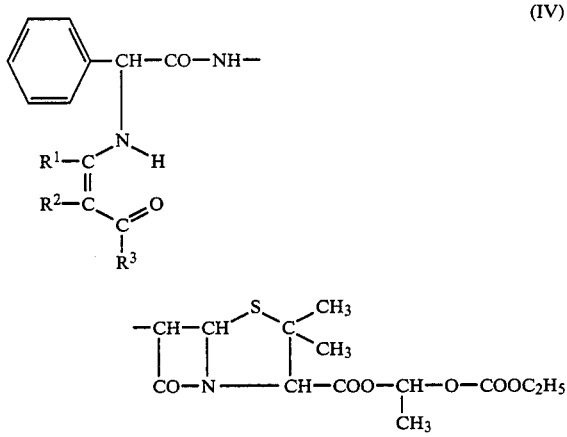 (IV)

wherein R¹, R² and R³ have the meanings specified above, and (c) mild hydrolysis in an acid medium to obtain the compound of formula (I).

2. Process according to claim 1, characterized by the fact that the formation of the ester in step (b) is carried out in the presence of a cataylst.

3. Process according to claim 2, characterized by the fact that the said catalyst is selected from the groups consisting of quaternary ammonium salts, alkali metal bromides, alkali metal iodides and cyclic ethers.

4. A process for the preparation of the 1-ethoxycarbonyloxyethyl ester of the 6-(D-(−)-α-amino-α-phenylacetamido)penicillanic acid with the formula:

comprising the steps of:

(a) in the presence of a material selected from the group consisting of an organic base and an alkaline carbonate in an aprotic solvent selected from the group consisting of N,N-dimethylacetamide, N,N-dimethylformamide, dimethoxyethane, dimethylsulphoxide, tetrahydrofuran and dioxane at a temperature between 0° C. and 60° C. for between 2 to 8 hours reacting ampicillin, or an alkaline salt, with a reactive derivative of acetoacetic acid to form the corresponding enamine with the formula:

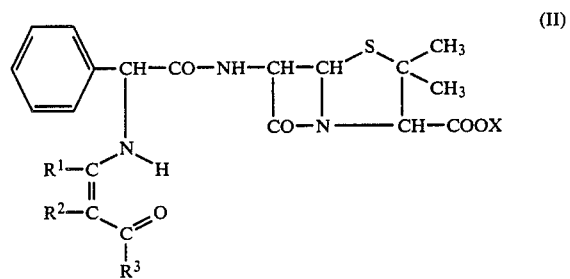 (II)

wherein R¹ represents an alkyl group containing 1–4 carbon atoms, a substituted or non-substituted aryl group or an aralkyl group; R² represents hydrogen, an alkyl group containing 1–4 carbon atoms, a substituted or non-substituted aryl group or an aralkyl group; R³ represents an alkyl group containing 1–4 carbon atoms, a substituted or non-substituted aryl group, an aralkyl group, an alkoxy group containing 1–4 carbon atoms, an aryloxy group or an amine group, and X represents an alkali metal, an alkaline earth metal or an organic base; and (b) reacting the resulting intermediate (II) in the presence of a catalyst with a compound of the formula (V)

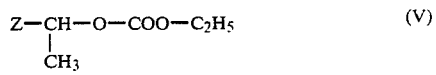 (V)

wherein Z is Cl or I.

5. Process according to claim 4, characterized in that the said catalyst is selected from the group consisting of quaternary ammonium salts, alkali metal bromides and iodides and cyclic ethers.

6. Process according to claim 3 wherein the catalyst is tetrabutylammonium bromide.

7. Process according to claim 5 wherein the catalyst is tetrabutylammonium bromide.

8. Process according to claim 2, 3, 4, 5, 6 or 24 characterized in that the catalyst is present in an amount of from 0.005 to 0.10 moles.

9. Process according to claim 8, wherein the catalyst is present in an amount from 0.01 to 0.10 moles.

10. A process for the preparation of the ethoxycarbonyloxyethyl ester of compounds selected from the group consisting of 6-aminopenicillanic acid, penicillins and cephalosporin which comprises the steps of (a) reacting a compound selected from the group consisting of 6-aminopenicillanic acid, penicillin and cephalosporin or a salt thereof with a reactive derivative of acetoacetic acid to form the corresponding enamine in the presence of a material selected from the group consisting of an organic base and an alkaline carbonate in an aprotic solvent selected from the group consisting of N,N-dimethylacetamide, N,N-dimethylformamide, dimethoxyethane, dimethylsulphoxide, tetrahydrofuran and dioxane at a temperature between 0° C. and 60° C. for between 2 to 8 hours, (b) reacting the resulting enamine intermediate with α-bromo-diethyl carbonate at a temperature of 15°–80° C. for 1–24 hours to form the corresponding ester, and (c) mildly hydrolysing the resulting compound in an acid medium to obtain the ethoxycarbonyloxyethyl ester.

* * * * *